United States Patent [19]
Cosmo et al.

[11] Patent Number: 6,051,732
[45] Date of Patent: Apr. 18, 2000

[54] PROCESS FOR THE PREPARATION OF 3-ACETOXY-2-METHYLBENZOYL CHLORIDE

[75] Inventors: Robert Cosmo, Darmstadt; Andreas Dierdorf, Frankfurt, both of Germany

[73] Assignee: Clariant GmbH, Frankfurt, Germany

[21] Appl. No.: 09/114,604

[22] Filed: Jul. 13, 1998

[30] Foreign Application Priority Data

Jul. 17, 1997 [DE] Germany ............... 197 30 602

[51] Int. Cl.$^7$ ............................... C07C 69/017
[52] U.S. Cl. ........................................ 560/130
[58] Field of Search ............................ 560/130

[56] References Cited

U.S. PATENT DOCUMENTS

| | | | |
|---|---|---|---|
| 4,065,477 | 12/1977 | Padmanathan | 260/369 |
| 5,484,926 | 1/1996 | Dressman et al. | 546/114 |

FOREIGN PATENT DOCUMENTS

| | | |
|---|---|---|
| WO 95/09843 | 4/1995 | WIPO . |
| WO 95/21164 | 8/1995 | WIPO . |
| WO95/32185 | 11/1995 | WIPO . |
| WO 96/22287 | 7/1996 | WIPO . |
| WO 97/11937 | 4/1997 | WIPO . |

OTHER PUBLICATIONS

Richard J. Lewis, Sr., Hawley's Condensed Chemical Dictionary, 12th edition, pp. 910 and 1145, No month provided 1993.

XP–002085121—Dean et al.: "The Synthesis of Some New Phenols" J. Chem. Soc., No month provided 1961, pp. 2773–2779.

Cresp et al., J. Cheml Soc. PerkinTrans. 1,2435 (No month provided 1974).

Fieser et al., J. Amer. Chem. Soc., 58, 749 (No month provided 1936).

Moreau et al., Bull. Soc. Chim. Fr., 3427 (No month provided 1973).

Kulic et al., J. Gen. Chem. USSR (Engl.) 60,2118 (No month provided 1990).

Giacalone, Gazz. Chem. Ital., 65,840 (No month provided 1935).

*Primary Examiner*—Rosalynd Keys
*Attorney, Agent, or Firm*—Scott Hanf

[57] ABSTRACT

The present invention relates to a process for the preparation of 3-acetoxy-2-methylbenzoyl chloride by reacting an alkali metal salt of 3-aminonaph-thalene-1,5-disulfonic acid with alkali metal hydroxide and water in the weight ratio 1:(1 to 1.6):(1 to 1.6) at 220 to 320° C. to give the dialkali metal salt of the 3-hydroxy-2-methylbenzoic acid, separating off insoluble constituents from the reaction mixture, then adjusting the reaction mixture to a pH of 11.5 to 13.5 by addition of acid and reacting with acetic anhydride at −5 to +25° C., precipitating the 3-acetoxy-2-methylbenzoic acid by addition of acid, separating off the 3-acetoxy-2-methylbenzoic acid and reacting it with an inorganic acid chloride to give 3-acetoxy-2-methylbenzoyl chloride.

21 Claims, No Drawings

PROCESS FOR THE PREPARATION OF 3-ACETOXY-2-METHYLBENZOYL CHLORIDE

BACKGROUND OF THE INVENTION

The present invention relates to an advantageous process for the preparation of 3-acetoxy-2-methylbenzoyl chloride.

3-Acetoxy-2-methylbenzoyl chloride is an important precursor for the preparation of pharmaceutical active compounds. In particular, it can be used as a structural unit for novel highly active HIV protease inhibitors, which inhibit the biological activity of the HIV protease enzyme. As a result of the inhibition of the biological activity of the HIV protease enzyme, the replication of the HIV virus is suppressed. In this way, novel possibilities of treatment of the immunodeficiency disease AIDS result. The preparation of an active compound of this type, which in the end is a decahydroisoquinoline derivative, is described in WO 95/09843. As is evident from Example 82 of WO 95/09843, [3S-(3R*, 4aR*, 8aR*, 2'S*, 3'R*)]-2-[3'-amino-2'-hydroxy-4'-phenyl]butyl decahydroisoquinoline-3-N-t-butylcarboxamide is reacted with 3-acetoxy-2-methylbenzoic acid in the presence of a dehydrating agent. The reaction proceeds at room temperature over a period of time of 2 days and leads to the formation of an amide bond between the 3-acetoxy-2-methylbenzoic acid and the primary amino group of the abovementioned decahydroisoquinoline.

The disadvantage of this synthesis is the rather long reaction time, the use of a dehydrating agent as well as a yield of only 65%.

With respect to the preceding explanations, the object is to prepare a substance whose use leads to a simplification of the synthesis and which can also be prepared on an industrial scale with justifiable expenditure.

This object is achieved by a process for the preparation of 3-acetoxy-2-methylbenzoyl chloride

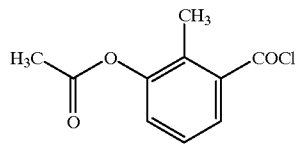

The abovementioned disadvantages can be avoided by reacting the abovementioned decahydroisoquinoline with 3-acetoxy-2-methylbenzoyl chloride. The good reactivity of 3-acetoxy-2-methylbenzoyl chloride advantageously results in a marked reduction of the reaction time. Moreover, the use of a dehydrating agent, such as the dicyclohexylcarbodiimide used in Example 82 of WO 95/09843, can be dispensed with entirely.

A further advantage is the high purity of the 3-acetoxy-2-methyl-benzoyl chloride, which can be purified in a simpler and better manner than 3-acetoxy-2-methylbenzoic acid.

Whereas 3-acetoxy-2-methylbenzoic acid can only be purified by complicated recrystallization, 3-acetoxy-2-methylbenzoyl chloride can be purified with low expenditure by fractional distillation.

An additional advantage to be mentioned is that the product losses in a comparatively simple fractional distillation are lower than in a labor-intensive recrystallization.

As already mentioned previously, the present invention relates to a process for the preparation of 3-acetoxy-2-methylbenzoyl chloride.

WO 95/09843 describes a multistage process for the preparation of 3-acetoxy-2-methylbenzoic acid. This process starts from 3-methoxybenzoyl chloride. The 3-methoxybenzoyl chloride is reacted with aniline to give 3-methoxy-N-phenylbenzamide. In a second step, the 3-methoxy-N-phenylbenzamide is reacted with 2 equivalents of n-butyllithium and then alkylated using methyl iodide. 3-Methoxy-2-methyl-N-phenylbenzamide is formed here, which is then reacted with aqueous hydrochloric acid and aqueous hydrogen bromide in boiling acetic acid with hydrolysis of the amide group and cleavage of the methoxy group to give 3-hydroxy-2-methylbenzoic acid. The 3-hydroxy-2-methylbenzoic acid must be acylated with acetic anhydride in order to obtain the 3-acetoxy-2-methylbenzoic acid. The individual reaction steps are described in greater detail in WO 95/09843 under Preparation 9 A, B and C and Example 81.

This synthesis route has several disadvantages. On the one hand, the reaction with n-butyllithium has to be carried out at rather low temperatures. As is evident from Preparation 9 B, the temperatures are in the range from −70 to −15° C. Low temperatures of this type can only be achieved on an industrial scale with very high expenditure.

On the other hand, the use of lithium alkyls is generally not unproblematical and necessitates working cautiously and carefully with this very reactive class of substance. Handling on an industrial scale requires particular safety measures and additional expenditure on apparatus.

Furthermore, the use of aggressive substances such as hydrochloric acid and hydrogen bromide leads to materials problems, since the reaction equipment has to be sufficiently resistant to corrosion by this substance. This can only be achieved by expensive materials.

Moreover, problems result in the disposal of waste gases and effluents polluted with hydrogen chloride and hydrogen bromide. Since neither hydrogen chloride nor hydrogen bromide must pass into the environment, they have to be specifically removed from the waste gases and effluents.

SUMMARY OF THE INVENTION

The process according to the invention for the preparation of 3-acetoxy-2-methylbenzoyl chloride avoids these disadvantages. It comprises reacting an alkali metal salt of 3-aminonaphthalene-1,5-di-sulfonic acid with alkali metal hydroxide and water in the weight ratio 1:(1 to 1.6):(1 to 1.6) at 220 to 320° C. to give the dialkali metal salt of 3-hydroxy-2-methylbenzoic acid, separating off insoluble constituents from the reaction mixture, then adjusting the reaction mixture to a pH of 11.5 to 13.5 by addition of acid and reacting it with acetic anhydride at −5 to 25° C., precipitating the 3-acetoxy-2-methylbenzoic acid by addition of acid, separating off the 3-acetoxy-2-methylbenzoic acid and reacting it with an inorganic acid chloride to give 3-acetoxy-2-methylbenzoyl chloride.

DESCRIPTION OF THE PREFERRED EMBODIMENTS

For easier understanding, the reaction steps in the following reaction scheme starting from the disodium salt of 3-aminonaphthalene-1,5-di-sulfonic acid as an alkali metal salt of 3-aminonaphthalene-1,5-disulfonic acid (1) and use of sodium hydroxide as an alkali metal hydroxide are shown here in simplified form.

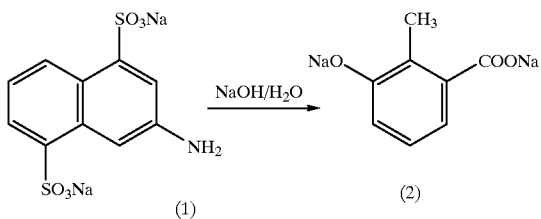

The disodium salt of 3-hydroxy-2-methylbenzoic acid (2) is reacted with acetic anhydride without intermediate isolation to give 3-acetoxy-2-methylbenzoic acid (3)

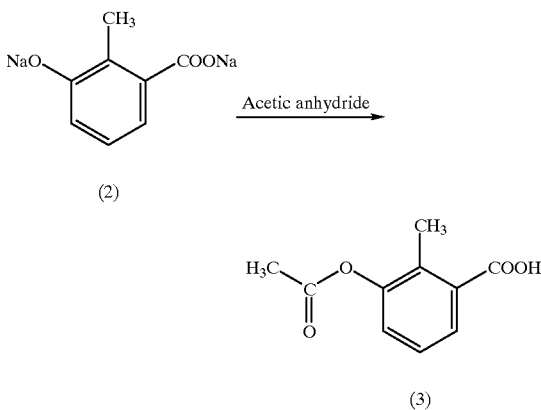

The 3-acetoxy-2-methylbenzoic acid (3) is then reacted, for example with thionyl chloride, to give 3-acetoxy-2-methylbenzoyl chloride (4)

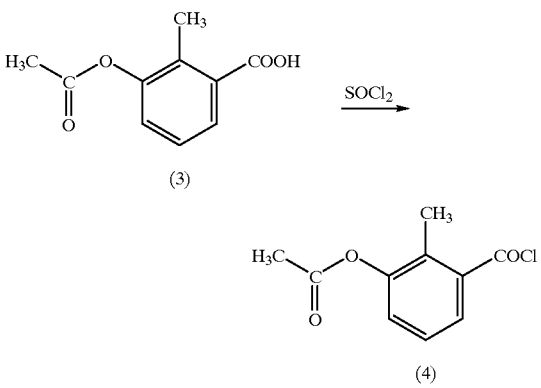

The advantages of the process according to the invention consist in a short sequence of reaction steps. Furthermore, a separation or isolation of the alkali metal salt of the 3-hydroxy-2-methylbenzoic acid can be dispensed with and the reaction with acetic anhydride can be carried out directly with the reaction product freed from insoluble constituents and adjusted to a prespecified pH.

It can be regarded as surprising that the reaction of the alkali metal salt of 3-aminonaphthalene-1,5-disulfonic acid can be carried out with markedly lower amounts of alkali metal hydroxide and markedly shorter reaction times than indicated by Dean et al., J. Chem. Soc. [1961] page 2775 without having to accept a significant decrease in the yield.

In this manner, the reactor can be better utilized, as the mixture employed essentially contains more alkali metal salts of 3-aminonaphthalene-1,5-disulfonic acid and the reaction time is shorter. Moreover, fewer waste products are obtained in the form of salts and also less acid is needed for the neutralization of the alkali metal melting and liberation of the 3-acetoxy-2-methylbenzoic acid.

Alkali metal salts of aminonaphthalene-1,5-disulfonic acid is understood as meaning a monoalkali metal salt or a dialkali metal salt of 3-aminonaphthalene-1,5-disulfonic acid or a mixture of these salts, in particular a monoalkali metal salt of 3-aminonaphthalene-1,5-disulfonic acid.

A monosodium, monopotassium, disodium or dipotassium salt of 3-aminonaphthalene-1,5-disulfonic acid or a mixture of these salts, in particular a monosodium or disodium salt of 3-aminonaphthalene-1,5-di-sulfonic acid or a mixture of these salts, is customarily employed.

In many cases, it has proven expedient to employ the monosodium salt or disodium salt, in particular the monosodium salt of 3-aminonaphthalene-1,5-disulfonic acid, as the alkali metal salt of 3-aminonaphthalene-1,5-di-sulfonic acid.

It is also possible to employ the free 3-aminonaphthalene-1,5-disulfonic acid. By reaction with alkali metal hydroxide, the corresponding alkali metal salt is formed, which is the actual starting material for the preparation of the dialkali metal salt of 3-hydroxy-2-methylbenzoic acid.

It has proven expedient to react the alkali metal salt of 3-aminonaphthalene-1,5-disulfonic acid with alkali metal hydroxide and water in the weight ratio 1:(1 to 1.5):(1 to 1.5), in particular 1:(1 to 1.4):(1 to 1.4).

It is possible to work to good effect with an excess of alkali metal hydroxide and water. In this case, it is recommended to react the alkali metal salt of the 3-aminonaphthalene-1,5-disulfonic acid with alkali metal hydroxide and water in the weight ratio 1:(1.1 to 1.5):(1.1 to 1.5), in particular 1:(1.2 to 1.4):(1.2 to 1.4).

The alkali metal hydroxide employed is sodium hydroxide, potassium hydroxide or a mixture thereof, in particular sodium hydroxide. The process turns out to be particularly simple if an aqueous solution of the alkali metal hydroxide is used.

The alkali metal salt of the 3-aminonaphthalene-1,5-disulfonic acid is reacted, as already mentioned previously, at 220 to 320° C., in particular at 250 to 300, preferably 260 to 290° C., with the alkali metal hydroxide and water to give the dialkali metal salt of 3-hydroxy-2-methylbenzoic acid.

The dialkali metal salt of 3-hydroxy-2-methylbenzoic acid can be, depending on which alkali metal salt of 3-aminonaphthalene-1,5-disulfonic acid and which alkali metal hydroxide was employed, a disodium salt, dipotassium salt or any desired mixture of sodium- and potassium-containing salts of 3-hydroxy-2-methylbenzoic acid.

If a sodium salt is employed as the alkali metal salt of the 3-aminonaphthalene-1,5-disulfonic acid and sodium hydroxide as the alkali metal hydroxide, the disodium salt of the 3-hydroxy-2-methylbenzoic acid is obtained. As is evident from formula (2), the one sodium ion is to be allocated to the carboxylic acid group and the other to the phenolate radical.

After reaction has taken place, the reaction mixture containing the dialkali metal salt of the 3-hydroxy-2-methylbenzoic acid is allowed to cool and the insoluble constituents are separated off at a temperature from 0 to 50, in particular 15 to 35° C.

The insoluble constituents can be separated off by centrifugation or filtration, in particular by filtration using a filter aid. Filter aids are understood as meaning chemically indifferent, insoluble compositions which lead to the formation of a loose, easily removable filter cake and prevent the blockage of the filter or of the filter cake or the passage of fine precipitates during the filtration. Filter aids which can be used are, for example, asbestos, kieselguhr, cellulose and cellulose derivatives.

The insoluble constituents are probably inorganic alkali metal salts, which unfavorably affect the subsequent further processing.

The reaction mixture freed from the insoluble constituents is adjusted to a pH of 11.5 to 13.5, in particular 11.8 to 13, by addition of acid, in particular by addition of a mineral acid.

Hydrochloric acid, acetic acid or sulfuric acid, in particular hydrochloric acid, is employed as an acid. The acid can be employed in concentrated form or in the form of a dilute aqueous solution.

In a large number of cases, it has proven expedient to react the reaction mixture adjusted to the desired pH with acetic anhydride at 0 to 20° C. A separation of the dialkali metal salt of 3-hydroxy-2-methylbenzoic acid or of the liberated 3-hydroxy-2-methylbenzoic acid can be dispensed with. The process according to the invention turns out to be particularly simple as a result.

Per mole of dialkali metal salt of 3-hydroxy-2-methylbenzoic acid, 1 to 5, in particular 1.1 to 3, preferably 1.3 to 2, mol of acetic anhydride are employed.

Customarily, the aqueous solution of the dialkali metal salt of 3-hydroxy-2-methylbenzoic acid is initially introduced and the acetic anhydride is metered in successively with stirring. After the end of the addition, the mixture is allowed to after-react for a certain time in order to complete the reaction.

During the reaction, the temperature is kept at the specified value by cooling.

After completion of the reaction, the reaction mixture is treated with an acid and the 3-acetoxy-2-methylbenzoic acid is precipitated. The acid used can be a mineral acid, in particular hydrochloric acid. In general, it is sufficient to precipitate the 3-acetoxy-2-methylbenzoic acid at a pH from 1 to 5, in particular 3 to 4, by adding sufficient acid to the reaction mixture until the desired pH in the abovementioned range is reached. The precipitate containing the 3-acetoxy-2-methylbenzoic acid is separated off, for example, by centrifugation or filtration, in particular by filtration, washed with water and the water is removed. The 3-acetoxy-2-methylbenzoic acid can be dried and processed further in the dry state. However, it is also possible to react the 3-acetoxy-2-methylbenzoic acid with the inorganic acid chloride in the moist state. In this case, the consumption of inorganic acid chloride, which reacts with the residual water still present, is higher than when using a dried 3-acetoxy-2-methylbenzoic acid.

If desired, the 3-acetoxy-2-methylbenzoic acid can be purified, for example by reprecipitation or recrystallization, before it is reacted with the inorganic acid chloride.

However, it is possible to dispense with an additional purification of the 3-acetoxy-2-methylbenzoic acid of this type and instead of this to further process the crude 3-acetoxy-2-methylbenzoic acid in the moist or dry state. The 3-acetoxy-2-methylbenzoic acid is obtained as a sufficiently pure crude product (content 95 to 99.5%, determined by HPLC analysis).

As a result of the use of crude 3-acetoxy-2-methylbenzoic acid, the process according to the invention turns out to be particularly simple, since a separate purification of the 3-acetoxy-2-methylbenzoic acid can be dispensed with. For this reason, this advantageous process variant is customarily preferred.

The 3-acetoxy-2-methylbenzoic acid is reacted with the inorganic acid chloride at 50 to 100, in particular 70 to 90° C., in the presence or absence, in particular in the absence, of an inert solvent.

Suitable solvents are, for example, heptane, diethyl ether, cyclohexane, toluene, o-xylene, m-xylene, p-xylene, mixtures of isomeric xylenes and hexane. However, it is possible to dispense with the use of a solvent. This variant is preferably used, as a rule, since it is particularly simple.

The 3-acetoxy-2-methylbenzoic acid is employed in the ratio 1:(1 to 5), in particular 1:(1.5 to 3), preferably 1:(2 to 2.5), to the chlorine present in the inorganic acid chloride and capable of exchange.

Chlorine capable of exchange is understood as meaning chlorine which substitutes the hydroxyl group in the carboxyl group of the carboxylic acid and leads to the formation of the corresponding carbonyl chloride.

The inorganic acid chloride employed is thionyl chloride, phosphorus trichloride or phosphorus pentachloride, in particular thionyl chloride or phosphorus trichloride, preferably thionyl chloride. Thionyl chloride and phosphorus pentachloride in each case have a chlorine capable of exchange. Accordingly, the 3-acetoxy-2-methylbenzoic acid is customarily reacted with thionyl chloride or phosphorus pentachloride in the molar ratio 1:(1 to 5), in particular 1:(1.5 to 3), preferably 1:(2 to 2.5).

Phosphorus trichloride has three chlorine substituents capable of exchange. Accordingly, the 3-acetoxy-2-methylbenzoic acid and phosphorus trichloride are reacted in the molar ratio 1:(0.3 to 1.5), in particular 1:(0.35 to 1), preferably 1:(0.4 to 0.6).

After completion of the reaction, the excess inorganic acid—if present—is distilled off. The 3-acetoxy-2-methylbenzoyl chloride can be obtained from the reaction mixture by fractional distillation under reduced pressure—depending on the distillation conditions selected—in a purity of 98.5 to 99.5%. The purity can be additionally increased, if desired, by, for example, again fractionally distilling the 3-acetoxy-2-methylbenzoyl chloride.

The inorganic acid chloride removed by distillation can be employed again in the reaction just like the solvent optionally removed.

The process according to the invention can be carried out batchwise or continuously, in particular batchwise.

The following example describes the invention in greater detail without restricting it.

EXAMPLES

Example 1

1a) Preparation of 3-acetoxy-2-methylbenzoic acid 100 g (0.31 mol) of monosodium salt of 3-aminonaphthalene-1,5-disulfonic acid and 200 g of a 50% by weight sodium hydroxide-containing aqueous solution are initially introduced into a 500 ml Hastelloy autoclave which is equipped with a propeller stirrer. The suspension formed from the substances employed is reacted at 280° C. for 6 hours with stirring. The reaction mixture is then cooled to 25° C. and rinsed from the autoclave with addition of 100 ml of water.

The reaction mixture is then filtered with addition of 10 g of a silicate-based filter aid, whereby the insoluble constituents are removed from the reaction mixture.

The yield of disodium salt of 3-hydroxy-2-methylbenzoic acid is 73% (determined by HPLC analysis).

A pH of 12.5 is set by addition of concentrated hydrochloric acid. The solution is then cooled to 0° C. and 68.1 g (0.67 mol) of acetic anhydride are added dropwise with stirring in the course of 15 minutes to the aqueous solution containing the disodium salt of the 3-hydroxy-2-methylbenzoic acid. The mixture is allowed to after-react with stirring for 15 minutes. The temperature is kept at 0° C. by cooling during the addition of acetic anhydride and during the after-reaction.

A pH of 3.8 is then set by addition of concentrated hydrochloric acid. The acetoxy-2-methylbenzoic acid precipitates as a solid, and is filtered off, washed with water and dried. 33.8 g of 3-acetoxy-2-methylbenzoic acid are obtained in a purity of 95% (determined by HPLC analysis). This corresponds to a yield of 60%, based on monosodium salt of 3-amino-naphthalene-1,5-disulfonic acid employed.

If the crude 3-acetoxy-2-methylbenzoic acid is additionally to be purified, it can be recrystallized from ethyl acetate or toluene, it being recommended to add activated carbon and to filter the solution of 3-acetoxy-2-methyl-benzoic acid hot. In this manner 3-acetoxy-2-methylbenzoic acid is obtained in a purity of 99.7% (determined by HPLC analysis).

1b) Preparation of 3-acetoxy-2-methylbenzoyl chloride 31.1 g (0.16 mol) of the crude 3-acetoxy-2-methylbenzoic acid (95% as obtained in Example 1a) and 36.0 g (0.30 mol) of thionyl chloride are initially introduced into a 250 ml four-necked flask which is equipped with a thermometer, reflux condenser and magnetic stirrer. The mixture is stirred and heated to reflux. The gases formed (HCl, $SO_2$) are passed into aqueous sodium hydroxide solution.

When the evolution of gas subsides, the excess thionyl chloride is distilled off. It can be reused for further reactions. The residue is distilled over a distillation bridge at 119 to 122° C. and 3 mbar. 25.6 g of 3-acetoxy-2-methylbenzoyl chloride are obtained in a purity of 98.5% (determined by GC analysis as methyl 3-acetoxy-2-methylbenzoate). This corresponds to a yield of 75.2%, based on 3-acetoxy-2-methylbenzoic acid employed.

| 3-Acetoxy-2-methylbenzoyl chloride: | |
|---|---|
| M.p: | 35.2° C. |
| MS: m/e | 214, 212 [M$^+$], 177 [M—Cl], 170 [M—CH$_3$CO], 135 ([M—Cl—CH$_3$CO], 100 %) |
| IR (KBr):/cm$^{-1}$ | 3400 w, 3000 w, 1775 vs, 1440 m, 1370 m, 1210 vs, 1185 vs, |
| $^1$H-NMR:/ppm | (CDCl$_3$; 60 MHz) |
| | δ = 2.33 (m, 6H, two methyl groups) |
| | δ = 7.1–7.5 (m, 2H, aromatic protons) |
| | δ = 7.9–8.4 (m, 1H, aromatic proton) |
| $^{13}$C-NMR:/ppm | (DMSO-d$_6$; 100 MHZ) |
| | δ = 13; 20.5; 126; 127; 127.5; 131; 133; 149; 168; 169 |

What is claimed is:

1. A process for the preparation of 3-acetoxy-2-methylbenzoyl chloride, which comprises reacting an alkali metal salt of 3-aminonaphthalene-1,5-disulfonic acid with alkali metal hydroxide and water in the weight ratio 1:(1 to 1.6):(1 to 1.6) at 220 to 320° C. to give the dialkali metal salt of 3-hydroxy-2-methylbenzoic acid, separating off insoluble constituents from the reaction mixture, then adjusting the reaction mixture to a pH of 11.5 to 1:3.5 by addition of acid and reacting it with acetic anhydride at −5 to 25° C., precipitating the 3-acetoxy-2-methylbenzoic acid by addition of acid, separating off the 3-acetoxy-2-methylbenzoic acid and reacting it with an inorganic acid chloride to give 3-acetoxy-2-methylbenzoyl chloride.

2. The process as claimed in claim 1, wherein the alkali metal salt of the 3-aminonaphthalene-1,5-disulfonic acid is reacted with alkali metal hydroxide and water in the weight ratio 1:(1 to 1.5):(1 to 1.5).

3. The process as claimed in claim 1, wherein the alkali metal hydroxide employed is sodium hydroxide, potassium hydroxide or a mixture thereof.

4. The process as claimed in claim 1, wherein the alkali metal hydroxide employed is sodium hydroxide.

5. The process as claimed in claim 1, wherein the alkali metal salt of the 3-aminonaphthalene-1,5-disulfonic acid is reacted at 250 to 300° C.

6. The process as claimed in claim 1, wherein the alkali metal salt of the 3-aminonaphthalene-1,5-disulfonic acid is reacted at 260 to 290° C.

7. The process as claimed in claim 1, wherein the insoluble constituents are removed from the reaction mixture at 0 to 50° C.

8. The process as claimed in claim 1, wherein the insoluble constituents are removed from the reaction mixture by centrifugation or filtration.

9. The process as claimed in claim 1, wherein the reaction mixture is adjusted to a pH of 11.5 to 13.5 by addition of a mineral acid as an acid.

10. The process as claimed in claim 1, wherein hydrochloric acid, acetic acid or sulfuric acid is employed as the acid.

11. The process as claimed in claim 1, wherein hydrochloric acid is employed as the acid.

12. The process as claimed in claim 1, wherein reaction with acetic anhydride is carried out at 0 to 20° C.

13. The process as claimed in claim 1, wherein 1 to 5 mol of acetic anhydride are employed per mole of dialkali metal salt of the 3-hydroxy-2-methylbenzoic acid.

14. The process as claimed in claim 1, wherein the 3-acetoxy-2-methylbenzoic acid is precipitated by addition of a mineral acid as the acid.

15. The process as claimed in claim 1, wherein the 3-acetoxy-2-methylbenzoic acid is precipitated at a pH of 1 to 5.

16. The process as claimed in claim 1, wherein the 3-acetoxy-2-methylbenzoic acid is reacted with the acid chloride at 50 to 100° C., in the presence or absence of an inert solvent.

17. The process as claimed in claim 1, wherein the 3-acetoxy-2-methylbenzoic acid is reacted in the ratio 1:(1 to 5) to the chlorine present in the inorganic acid chloride and capable of exchange.

18. The process as claimed in claim 1, wherein thionyl chloride, phosphorus trichloride or phosphorus pentachloride is employed as the inorganic acid chloride.

19. The process as claimed in claim 15 wherein the 3-acetoxy-2-methylbenzoic acid is precipitated at a pH of 3 to 4.

20. The process as claimed in claim 16, wherein the 3-acetoxy-2-methylbenzoic acid is reacted with the inorganic acid chloride at 70 to 90° C., in the presence or absence of an inert solvent.

21. The process as claimed in claim 17, wherein the 3-acetoxy-2-methylbenzoic acid is reacted in the ratio 1:(1.5 to 3) to the chlorine present in the inorganic acid chloride and capable of exchange.

* * * * *

UNITED STATES PATENT AND TRADEMARK OFFICE
CERTIFICATE OF CORRECTION

PATENT : 6,051,732

DATED : April 18, 2000

INVENTOR(S) : Robert Cosmo and Andreas Dierdorf

It is certified that error appears in the above-identified patent and that said Letters Patent is hereby corrected as shown below:

Column 7,
in Claim 1, line 8, "11.5 to 1:3.5" should read -- 11.5 to 13.5 --

Signed and Sealed this

Twentieth Day of March, 2001

Attest:

NICHOLAS P. GODICI

*Attesting Officer*                *Acting Director of the United States Patent and Trademark Office*